Aug. 29, 1950 F. MEILLAND Plant Pat. 977
ROSE PLANT
Filed Aug. 18, 1949
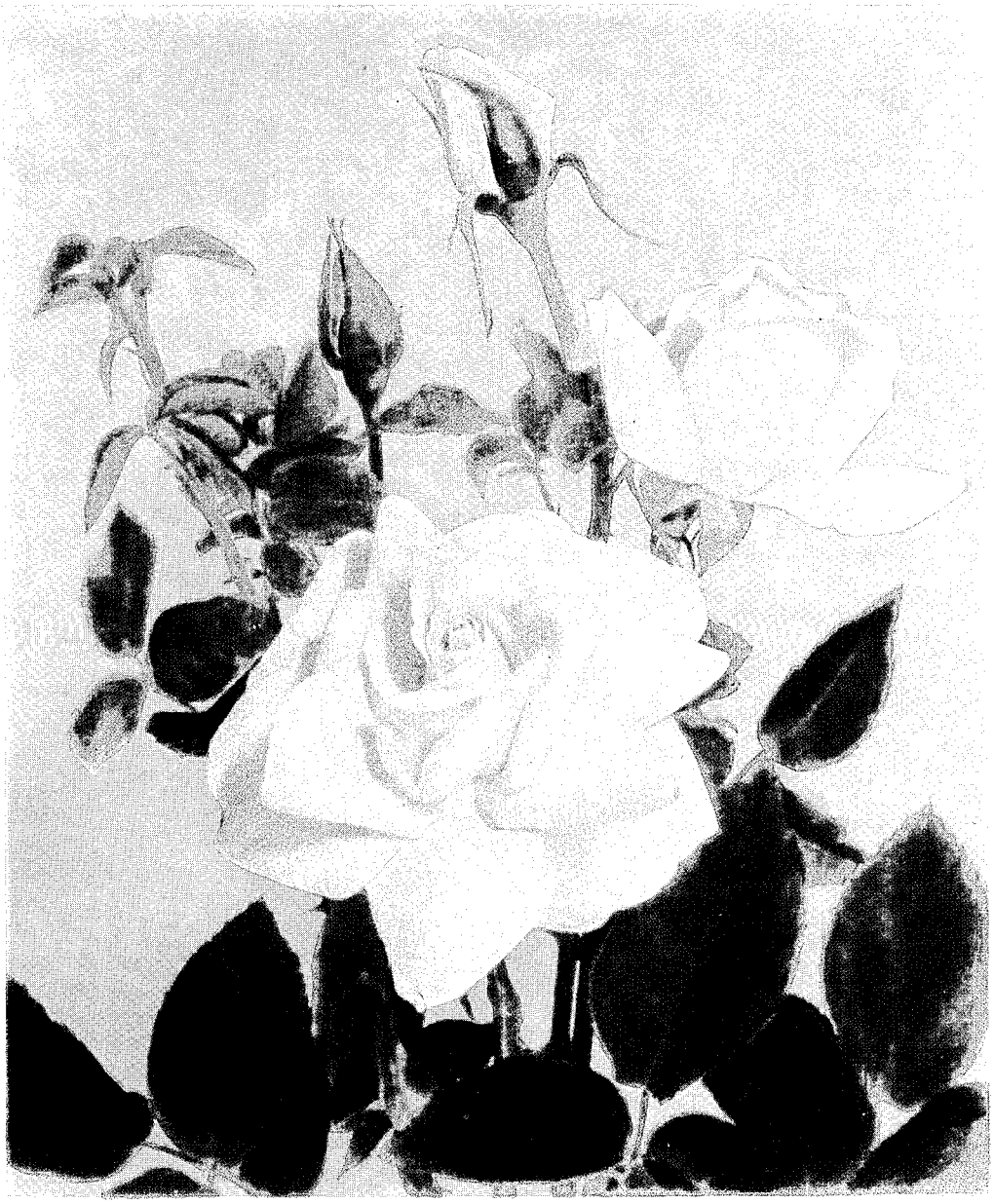
Inventor
F. Meilland
By Robbins Robb
Attorneys Patented Aug. 29, 1950 Plant Pat. 977

UNITED STATES PATENT OFFICE

977

ROSE PLANT

Francis Meilland, Cap Azura, Cap d'Antibes, France, assignor to The Conard-Pyle Company, West Grove, Pa., a corporation of Pennsylvania Application August 18, 1949, Serial No. 110,952

1 Claim. (Cl. 47—61)

The present invention relates to a new and distinct variety of rose plant, the dominating characteristics of which are the distinctive two-tone color of the blooms, the large and classic form of the buds and its abundant foliage. This plant is particularly notable for its production of a desirable quantity of the unusual, highly colored, blooms which adapt it for use both for cut flower purposes and garden decoration.

Asexual reproduction of this new variety shows the foregoing characteristics come true to form and are established.

In the drawings are shown specimens of the new variety at different stages of development of both the blossoms and the foliage.

This new variety was asexually reproduced at West Grove, Pennsylvania, by budding.

The following is a detailed description of the new variety, reference to color being in accordance with Ridgway's Color Standards and Nomenclature where indicated and otherwise in accordance with the usual dictionary meaning:

Type: Hardy; bush; outdoor; seedling; for cut flowers and garden decoration.

Class: Hybrid tea.

Parentage: An unnamed seedling of Joanna Hill crossed with an unnamed seedling of Mme. Joseph Perraud.

Propagation: Holds its distinguishing characteristics through succeeding propagations.

*Flower*

Locality where grown: West Grove, Pennsylvania.

Flowers borne: Singly to stem; on normal, medium length stems.

Quantity of bloom: Moderate to free outdoors.

Continuity: Continuous.

Fragrance: Moderate; spicy.

Bud:

*Peduncle.*—Medium heavy; erect; stiff; medium rough; several green prickles. Color—Lettuce Green, Plate V.

*Before calyx breaks.*—Size—medium. Form—Pointed; with foliaceous appendages on the surface of the bud; with slender, cut foliaceous parts extending beyond the tip of the bud equal to one-fourth or more of its length.

*As calyx breaks.*—Color—Light Coral Red, Plate XIII, to Coral Red, Plate XIII.

*As first petal opens.*—Size—medium. Form—long; pointed. Color—Outside: Strawberry Pink, Plate I; inside: Lemon Chrome, Plate IV, at base shading to Capucine Yellow, Plate III, to Orange Buff, Plate III, at outer edge.

*Opening.*—Opens up well.

Bloom: Size, when fully open, Large; 4½ inches to 5 inches.

*Petalage.*—Double; from 25 to 35 petals; arranged regularly.

*Form.*—Very high center at first; becoming high centered; petals remaining at first very loosely rolled outward; becoming later, at maturity, loosely rolled outward.

Petals: Leathery; with inside satiny and outside satiny.

*Shape.*—Outside—obovate; apex pointed. Intermediate—obovate; apex pointed. Inside—obovate; apex pointed.

*Color.*—Colors may be modified by being shaded with other colors.

This description of a newly opened flower was made from a rose grown outdoors in the month of August, at West Grove, Pennsylvania:

*Color.*—*Outside petal*—outside surface: Peach Red, Plate I; inside surface: Ochraceous Buff, Plate XV, to Ochraceous Salmon, Plate XV. *Intermediate petal*—outside surface: Scarlet, Plate I; inside surface: Salmon Orange, Plate II. *Inner petal*—outside surface: Scarlet, Plate I; inside surface: Salmon Orange, Plate II.

This description was made from a rose that was open for three days outdoors in the month of August, at West Grove, Pennsylvania:

*Color.*—*Outside petal*—outside surface: Shading from Pale Greenish Yellow at base to white to Jasper Pink, Plate XIII, over most of petal; inside surface: Shading from Pale Greenish Yellow, Plate V, at base to Warm Buff, Plate XV, to Seashell Pink, Plate XIV, at outer edges. *Inside petal*—outside surface: Shading from Picric Yellow, Plate IV, at base to Bittersweet Pink, Plate II, and to Geranium Pink, Plate I; inside surface: Shading from Pinard Yellow, Plate IV, at base to Capucine Buff, Plate III, to Salmon Buff, Plate XIV, at outer edges. Occasionally with tinges of Jasper Red, Plate XIII.

*General color effect.*—Newly opened flower—Orange Buff, Plate III, with Coral Red, Plate XIII, at center. Three days open—Seashell Pink, Plate XIV, at outer edges of flower; Pale Orange Yellow, Plate III, over most of flower; sometimes Geranium Pink, Plate I, at very center.

*Behavior.*—Drop off cleanly.

*Flower longevity.*—Cut roses grown outdoors kept at living room temperatures 4 to 5 days in August.

*Reproductive organs*

Stamens: Medium number; mixed with petaloids.
Filaments: Medium length; most with anthers. Color—Pale Orange Yellow, Plate III, to Capucine Orange, Plate III.
Anthers: Rarely, an anther fused with a petaloid; medium size; all open at once. Color—Orange, Plate III, with Baryta Yellow, Plate IV, center stripe.
Pollen: Moderate. Color—Orange, Plate III.
Pistils: Medium number.
Styles: Uneven; medium length; medium heavy; bunched.
Stigma: Pinard Yellow, Plate IV.
Ovaries: Some protruding from calyx.
Hips: Short; moderately smooth; walls medium thin. Color—Courge Green, Plate XVII.
Sepals: Permanent; medium length; spear shaped.
Seeds: Few; medium size.

*Plant*

Foliage:
*Leaves.*—Compound of three or five leaflets; abundant; medium size; leathery.
*Leaflets.*—Ovoid with apex acute; base round; margin simply serrate.
*Color.* — *Mature* — upper surface: Jade Green, Plate XXXI; under surface: Vetiver Green, Plate XLVII. *Young*—upper surface: Yellowish Oil Green, Plate V, veiled with Walnut Brown, Plate XXVIII; under surface: Dark Vinaceous, Plate XXVII, with patches of Courge Green, Plate XVII.
*Rachis.* — Medium heavy. Upper side—grooved, hairy. Under side—sparsely thorny.

*Stipules.*—Medium length; medium width; medium length points, turning out at an angle of less than 90°.
*Disease.*—Resistant to mildew and blackspot.

Growth:
*Habit.*—Upright; branched moderately.
*Growth.*—Moderate.
*Canes.*—Medium heavy.
*Main stems.*—Gray-green. *Thorns*—many; short to medium length; hooked downward; with short narrow base. Incipient thorns among large. *Prickles*—several; red-brown. *Hairs*—none.
*Branches.*—Gray-green, often with reddish shadings. *Thorns.* — several; medium length; hooked downward; with medium length narrow base. *Prickles.*—several; gray. *Hairs.*—none.
*New shoots.*—Cosse Green, Plate V, sometimes shaded with red. *Thorns*—many; long; hooked downward with medium length narrow base. Incipient thorns among large ones. *Prickles* — several; some gray, some reddish. *Hairs*—none.

I claim:

A new and distinct variety of rose plant characterized as to novelty by the intensity of the ruddy-gold color tones of its blooms; by the large and classic rose form of its opening buds; its abundant foliage suitable for providing a contrasting background for the bright deep gold colored flowers, substantially as shown and described.

FRANCIS MEILLAND.

No references cited.